United States Patent
Kirt et al.

(10) Patent No.: US 12,239,796 B2
(45) Date of Patent: Mar. 4, 2025

(54) ELASTOMERIC STRAIN RELIEF LAYERING FOR CATHETERS

(71) Applicant: BOSTON SCIENTIFIC SCIMED, INC., Maple Grove, MN (US)

(72) Inventors: David Cory Kirt, Minnetonka, MN (US); Benjamin Mihelich, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 673 days.

(21) Appl. No.: 17/017,835

(22) Filed: Sep. 11, 2020

(65) Prior Publication Data
US 2021/0077777 A1    Mar. 18, 2021

Related U.S. Application Data

(60) Provisional application No. 62/899,844, filed on Sep. 13, 2019.

(51) Int. Cl.
*A61M 25/00*    (2006.01)

(52) U.S. Cl.
CPC . *A61M 25/0045* (2013.01); *A61M 2025/0059* (2013.01); *A61M 2205/0216* (2013.01)

(58) Field of Classification Search
CPC .............. A61M 25/09; A61M 25/0905; A61M 25/0102; A61M 25/0169;
(Continued)

(56) References Cited

U.S. PATENT DOCUMENTS

| 5,275,152 A | * | 1/1994 | Krauter | A61B 1/0052 |
| | | | | 600/129 |
| 5,460,608 A | * | 10/1995 | Lodin | A61M 25/104 |
| | | | | 604/103.09 |

(Continued)

FOREIGN PATENT DOCUMENTS

| EP | 2174685 B1 | 8/2012 |
| EP | 2572749 A2 | 3/2013 |

(Continued)

OTHER PUBLICATIONS

International Search Report and Written Opinion dated Dec. 23, 2020 for International Application No. PCT/US2020050444.

*Primary Examiner* — Emily L Schmidt
*Assistant Examiner* — Antarius S Daniel
(74) *Attorney, Agent, or Firm* — Seager, Tufte & Wickhem LLP (57) ABSTRACT

A medical device configured to be flexible and maintain kink resistance while also reducing strain fractures. The medical device may include an elongate tubular shaft defining a lumen extending from a proximal portion to a distal portion. The elongate tubular shaft may comprise an outer jacket forming an outer surface of the elongate tubular shaft, a support member including at least one filament extending in a helical configuration along at least a portion of the a length of the elongate tubular shaft, and a strain relief layer comprising a material that has a modulus of elasticity less than a modulus of elasticity of the outer jacket, the strain relief layer positioned at least between adjacent windings of the support member. The strain relief layer and the support member may collectively form an inner surface of the elongate tubular shaft.

4 Claims, 10 Drawing Sheets

(58) Field of Classification Search
CPC .......... A61M 25/09041; A61M 25/104; A61M 25/0054; A61M 25/0068; A61M 25/0108; A61M 25/0023; A61M 25/0012; A61M 25/0136; A61M 25/065; A61M 25/0606; A61M 25/0045; A61M 2025/0062; A61M 2025/0175; A61M 2025/0042; A61M 2025/0183; A61M 2025/0656

See application file for complete search history.

(56) References Cited

U.S. PATENT DOCUMENTS

| | | | |
|---|---|---|---|
| 5,947,940 | A | 9/1999 | Beisel |
| 9,067,332 | B2 | 6/2015 | Lippert et al. |
| 9,067,333 | B2 | 6/2015 | Lippert et al. |
| 9,072,873 | B2 | 7/2015 | Lippert et al. |
| 9,616,195 | B2 | 4/2017 | Lippert et al. |
| 10,695,531 | B2 * | 6/2020 | Suzuki ................ B29C 37/0053 |
| 2004/0002728 | A1 | 1/2004 | Speck et al. |
| 2005/0115624 | A1 * | 6/2005 | Walak ................ A61M 25/0009 138/139 |
| 2005/0271844 | A1 | 12/2005 | Mapes et al. |
| 2006/0253197 | A1 | 11/2006 | NaPier |
| 2007/0110935 | A1 | 5/2007 | Mapes et al. |
| 2010/0256602 | A1 | 10/2010 | Lippert et al. |
| 2010/0256603 | A1 | 10/2010 | Lippert et al. |
| 2010/0256604 | A1 | 10/2010 | Lippert et al. |
| 2012/0016344 | A1 | 1/2012 | Kusakabe |
| 2016/0067444 | A1 | 3/2016 | Allen et al. |
| 2016/0346503 | A1 * | 12/2016 | Jackson ............ A61M 25/0021 |
| 2017/0181653 | A1 | 6/2017 | Highsmith et al. |
| 2017/0291014 | A1 | 10/2017 | Royer et al. |
| 2018/0318551 | A1 * | 11/2018 | Wasdyke .......... A61M 25/0054 |
| 2022/0233814 | A1 * | 7/2022 | Mullins ............. A61M 25/0054 |

FOREIGN PATENT DOCUMENTS

| | | |
|---|---|---|
| EP | 2581104 A1 | 4/2013 |
| WO | 2005120622 A2 | 12/2005 |
| WO | 2010115163 A1 | 10/2010 |
| WO | 2010115163 A9 | 7/2011 |
| WO | 2014140093 A1 | 9/2014 |
| WO | 2015186692 A1 | 12/2015 |
| WO | 2017004194 A1 | 1/2017 |
| WO | 2017180639 A1 | 10/2017 |
| WO | 2018064325 A1 | 4/2018 |

* cited by examiner

ELASTOMERIC STRAIN RELIEF LAYERING FOR CATHETERS

CROSS-REFERENCE TO RELATED APPLICATIONS

This application claims the benefit of priority of U.S. Provisional Application No. 62/899,844 filed Sep. 13, 2019 the entire disclosure of which is hereby incorporated by reference.

TECHNICAL FIELD

The invention relates generally to medical devices and more particularly to catheters having strain relief layering.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

The disclosure is directed to several alternative designs, materials and methods of manufacturing medical device structures and assemblies.

In a first example, a medical device may comprise an elongate tubular shaft defining a lumen extending from a proximal portion to a distal portion. The elongate tubular shaft may comprise an outer jacket forming an outer surface of the elongate tubular shaft a support member, including at least one filament extending in a helical configuration along at least a portion of the a length of the elongate tubular shaft, and a strain relief layer comprising a material that has a modulus of elasticity less than a modulus of elasticity of the outer jacket. The strain relief layer may be positioned at least between adjacent windings of the support member. The strain relief layer and the support member may collectively form an inner surface of the elongate tubular shaft.

Alternatively or additionally to any of the examples above, in another example, the strain relief layer may have a thickness approximately equal to a thickness of the at least one filament in a radial direction.

Alternatively or additionally to any of the examples above, in another example, a thickness of the outer jacket may be generally uniform over a length of the elongate tubular shaft.

Alternatively or additionally to any of the examples above, in another example, the strain relief layer may be further disposed on a radially outward surface of the at least one filament.

Alternatively or additionally to any of the examples above, in another example, a thickness of the outer jacket may be variable over a length of the elongate tubular shaft.

Alternatively or additionally to any of the examples above, in another example, the strain relief layer may have a generally uniform thickness along a length of the elongate tubular shaft.

Alternatively or additionally to any of the examples above, in another example, the support member may comprise two or more filaments woven to form a braid.

Alternatively or additionally to any of the examples above, in another example, the strain relief layer may comprise an elastomeric material.

Alternatively or additionally to any of the examples above, in another example, the strain relief layer may comprise an elastomeric urethane.

Alternatively or additionally to any of the examples above, in another example, the strain relief layer may comprise an elastomeric polyether block amide.

Alternatively or additionally to any of the examples above, in another example, the outer jacket may comprise a polyamide.

Alternatively or additionally to any of the examples above, in another example, the outer jacket may comprise a polyether block amide having a durometer of about 63D or greater.

Alternatively or additionally to any of the examples above, in another example, the support member may comprise a metal or metal alloy.

Alternatively or additionally to any of the examples above, in another example, the support member may comprise a non-metallic material.

Alternatively or additionally to any of the examples above, in another example, the distal portion of the elongate tubular shaft may have a greater flexibility than the proximal portion of the elongate tubular shaft.

In another example, a medical device may comprise an elongate tubular shaft defining a lumen extending from a proximal portion to a distal portion. The elongate tubular shaft may comprise an outer jacket forming an outer surface of the elongate tubular shaft, a support member including at least one filament extending in a helical configuration along at least a portion of the a length of the elongate tubular shaft, and a strain relief layer comprising a material that has a modulus of elasticity less than a modulus of elasticity of the outer jacket. The strain relief layer may be positioned at least between adjacent windings of the support member. The strain relief layer and the support member may collectively form an inner surface of the elongate tubular shaft.

Alternatively or additionally to any of the examples above, in another example, the strain relief layer may have a thickness approximately equal to a thickness of the at least one filament in a radial direction.

Alternatively or additionally to any of the examples above, in another example, a thickness of the outer jacket may be generally uniform over a length of the elongate tubular shaft.

Alternatively or additionally to any of the examples above, in another example, the strain relief layer may be further disposed on a radially outward surface of the at least one filament.

Alternatively or additionally to any of the examples above, in another example, a thickness of the outer jacket may be variable over a length of the elongate tubular shaft.

Alternatively or additionally to any of the examples above, in another example, the strain relief layer may have a generally uniform thickness along a length of the elongate tubular shaft.

Alternatively or additionally to any of the examples above, in another example, the support member may comprise two or more filaments woven to form a braid.

Alternatively or additionally to any of the examples above, in another example, the strain relief layer may comprise an elastomeric material.

Alternatively or additionally to any of the examples above, in another example, the strain relief layer may comprise an elastomeric urethane.

Alternatively or additionally to any of the examples above, in another example, the strain relief layer may comprise an elastomeric polyether block amide.

Alternatively or additionally to any of the examples above, in another example, the outer jacket may comprise a polyamide.

Alternatively or additionally to any of the examples above, in another example, the outer jacket may comprise a polyether block amide having a durometer of about 63D or greater.

In another example, a medical device may comprise an elongate tubular shaft defining a lumen extending from a proximal portion to a distal portion. The elongate tubular shaft may comprise an outer jacket forming an outer surface of the elongate tubular shaft and having a thickness that is generally uniform over a length of the elongate tubular shaft, a support member including at least one filament extending in a helical configuration along at least a portion of the a length of the elongate tubular shaft, and a strain relief layer comprising a material that has a modulus of elasticity less than a modulus of elasticity of the outer jacket. The strain relief layer may be positioned at least between adjacent windings of the support member and having a thickness approximately equal to a thickness of the at least one filament in a radial direction. The strain relief layer and the support member may collectively form an inner surface of the elongate tubular shaft.

Alternatively or additionally to any of the examples above, in another example, the strain relief layer may comprise an elastomeric urethane.

Alternatively or additionally to any of the examples above, in another example, the strain relief layer may comprise an elastomeric polyether block amide.

Alternatively or additionally to any of the examples above, in another example, the outer jacket may comprise a polyamide or a polyether block amide having a durometer of about 63D or greater.

In another example, a medical device may comprise an elongate tubular shaft defining a lumen extending from a proximal portion to a distal portion. The elongate tubular shaft may comprise an outer jacket forming an outer surface of the elongate tubular shaft and having a thickness that is variable over a length of the elongate tubular shaft, a support member including at least one filament extending in a helical configuration along at least a portion of the a length of the elongate tubular shaft, and a strain relief layer comprising a material that has a modulus of elasticity less than a modulus of elasticity of the outer jacket. The strain relief layer may be positioned at least between adjacent windings of the support member and over a radially outward surface of the at least one filament. The strain relief layer and the support member may collectively form an inner surface of the elongate tubular shaft.

Alternatively or additionally to any of the examples above, in another example, the strain relief layer may comprise an elastomeric urethane.

Alternatively or additionally to any of the examples above, in another example, the strain relief layer may comprise an elastomeric polyether block amide.

Alternatively or additionally to any of the examples above, in another example, the outer jacket may comprise a polyamide or a polyether block amide having a durometer of about 63D or greater.

The above summary of some example embodiments is not intended to describe each disclosed embodiment or every implementation of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

The terms "proximal" and "distal" as used herein are intended to refer to a direction toward (proximal) and away from (distal) a user of the device.

Figure 1A:
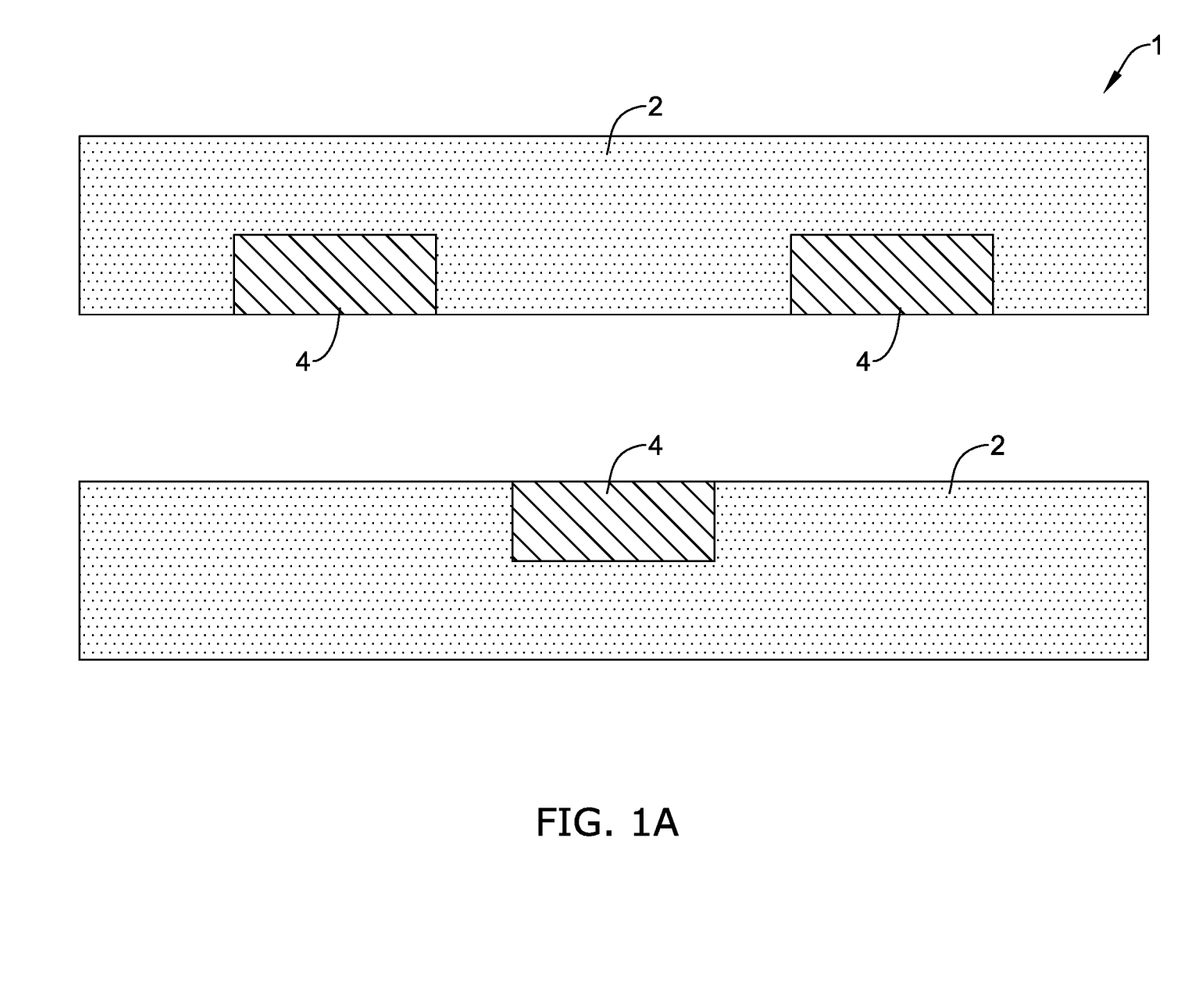
FIG. 1A is a partial sectioned view of a reinforced catheter.
Figure 1B:
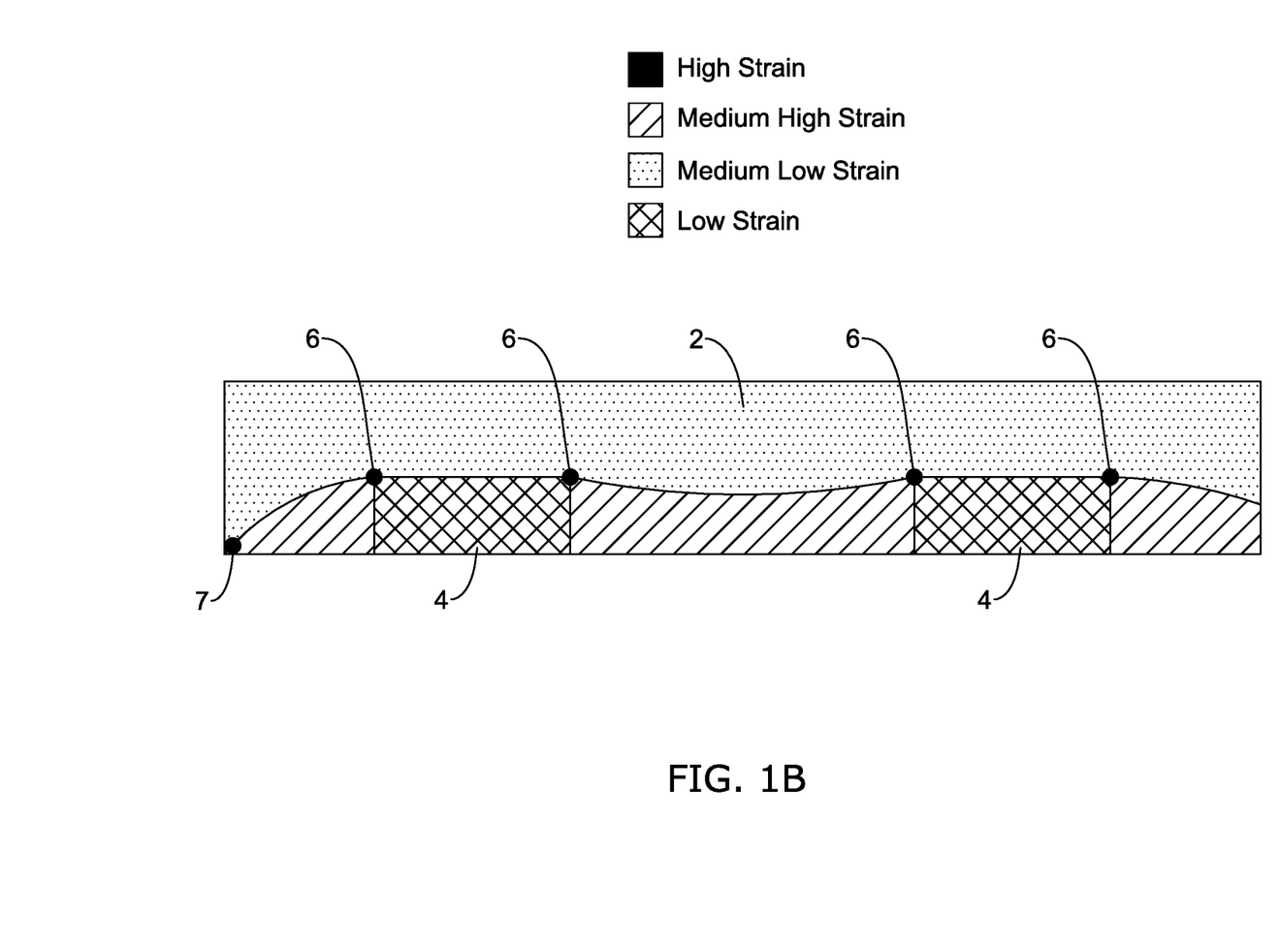
FIG. 1B is a schematic finite element analysis (FEA) of strain in the reinforced catheter of FIG. 1A.
Figure 1C:
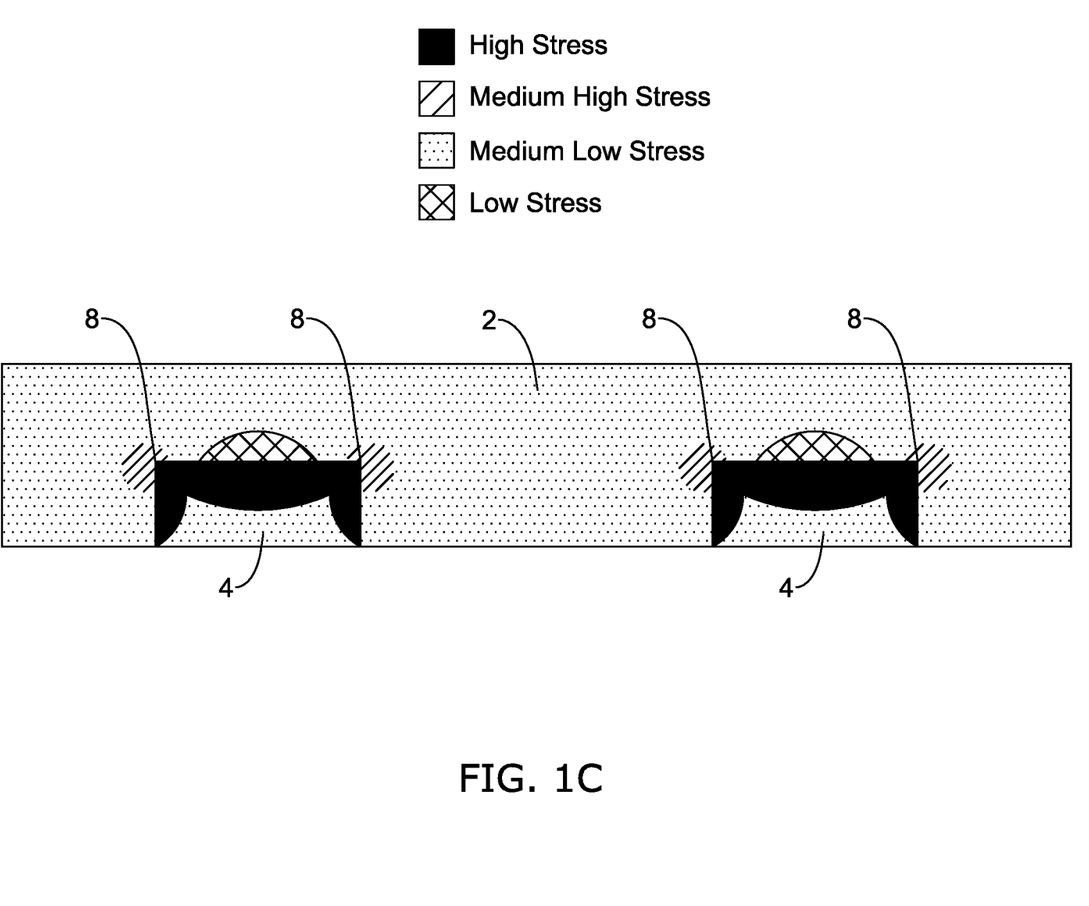
FIG. 1C is a schematic finite element analysis (FEA) of stress in the reinforced catheter of FIG. 1A.

To achieve a required flexibility and maintain kink resistance in thin walled polymer catheters, the catheter (or other elongate tubular shaft) may be reinforced with high modulus components such as, but not limited to, coils or braids to increase their hoop strength. FIG. 1A is a partial sectioned view of an illustrative catheter 1 having an elongate tubular shaft 2 and a high modulus component 4. The high modulus component 4 may be laminated into the wall of the elongate tubular shaft 2 which may allow for a smaller bend radius before kinking. However, the high modulus component 4 may create a failure mode where the side of the catheter wall that is in the highest tension and under the greatest strain fractures. FIG. 1B is a schematic finite element analysis (FEA) of strain in one side of the catheter 1 of FIG. 1A. FIG. 1C is a schematic finite element analysis (FEA) of stress in one side of the catheter 1 of FIG. 1A. As can be seen in FIGS. 1B and 1C, the highest strain 6 in the elongate tubular shaft 2 is at the upper corners of the high modulus component 4 and the highest stress 8 in the elongate tubular shaft 2 is at the corners of the high modulus component 4. Other regions 7 of high strain may occur within the elongate tubular shaft 2. The regions 7 may be at lower corners of the high modulus component 4, in a space between adjacent windings of the high modulus component, etc. However, in some cases, the onset of fracture may occur at stress corners 8 where the polymer is laminated onto the coil or the braid. This may be caused by geometry (e.g., sharp corners) and/or the significant different in material properties (e.g., Young's modulus) at the transition points. In some cases, the occurrence of fracture may increase with a polymer's notch sensitivity (e.g., the extent to which a material is prone to fracture in the presence of a surface inhomogeneity, which may include a change in material). Brittle materials may have a higher notch sensitivity than more ductile materials. What may be desirable is an elongate tubular shaft which is flexible and maintains kink resistance while also reducing strain fractures.

Figure 2:
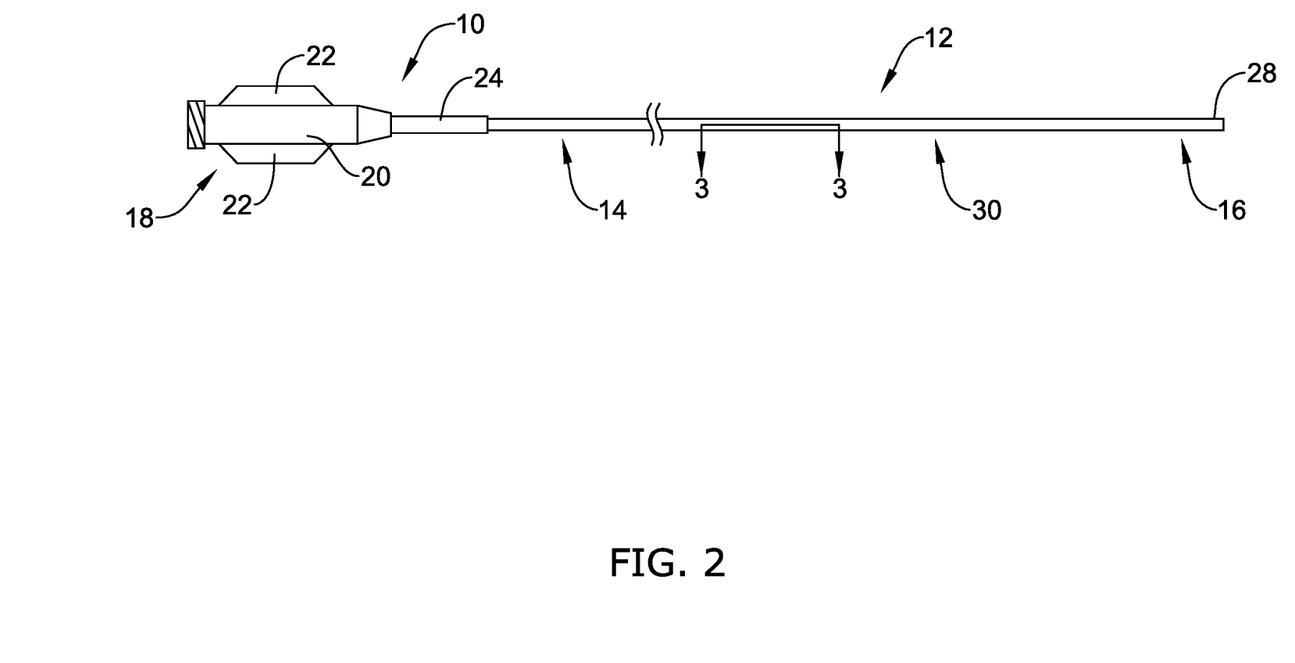
FIG. 2 is a plan view of a medical device in accordance with an embodiment of the invention.

FIG. 2 is a plan view of an illustrative medical device 10, for example, a catheter. The medical device 10 can be any of a variety of different catheters. In some embodiments, the medical device 10 can be an intravascular catheter. Examples of intravascular catheters include balloon catheters, atherectomy catheters, drug delivery catheters, diagnostic catheters and guide catheters. However, the medical device 10 may take the form of other suitable guiding, diagnosing, or treating devices (including catheters, endoscopic instruments, laparoscopic instruments, etc., and the like) and it may be suitable for use at other locations and/or body lumens within a patient. The medical device 10 can be sized in accordance with its intended use. For example, the medical device 10 can have a length that is in the range of about 50 to about 200 centimeters, about 75 to about 175 centimeters, or about 100 to about 150 centimeters. It is further contemplated that the diameter of the medical device 10 may vary based on the use application.

In the illustrated embodiment, the medical device 10 may include an elongate tubular shaft 12 that has a proximal portion 14, a distal portion 16 terminating at a distal end 28, and an intermediate region 30 disposed between the proximal portion 14 and the distal portion 16. The elongate tubular shaft 12 may extend proximally from the distal end 28 to the proximal portion 14 which may be configured to remain outside of a patient's body. Depending on the use application, a hub and strain relief assembly 18 can be connected to the proximal portion 14 of the elongate tubular shaft 12. The hub and strain relief assembly 18 may include a main body portion 20 for connecting other treatment devices or providing a port for facilitating other treatments and a strain relief 24 that is intended to reduce kinking. The hub and strain relief assembly 18 can also include a pair of flanges 22. The hub and strain relief assembly 18 can be of conventional design and can be attached using conventional techniques. Other hubs and/or handles can replace the hub and strain relief assembly 18 for different use cases.

While not explicitly shown, the elongate tubular shaft 12 can include one or more shaft segments having varying degrees of flexibility. In some cases, the elongate tubular shaft 12 may be progressively more flexible toward the distal end 28 thereof, although this is not required. It is contemplated that the stiffness and size of the elongate tubular shaft 12 may be modified for use in various locations within the body.

Figure 3:
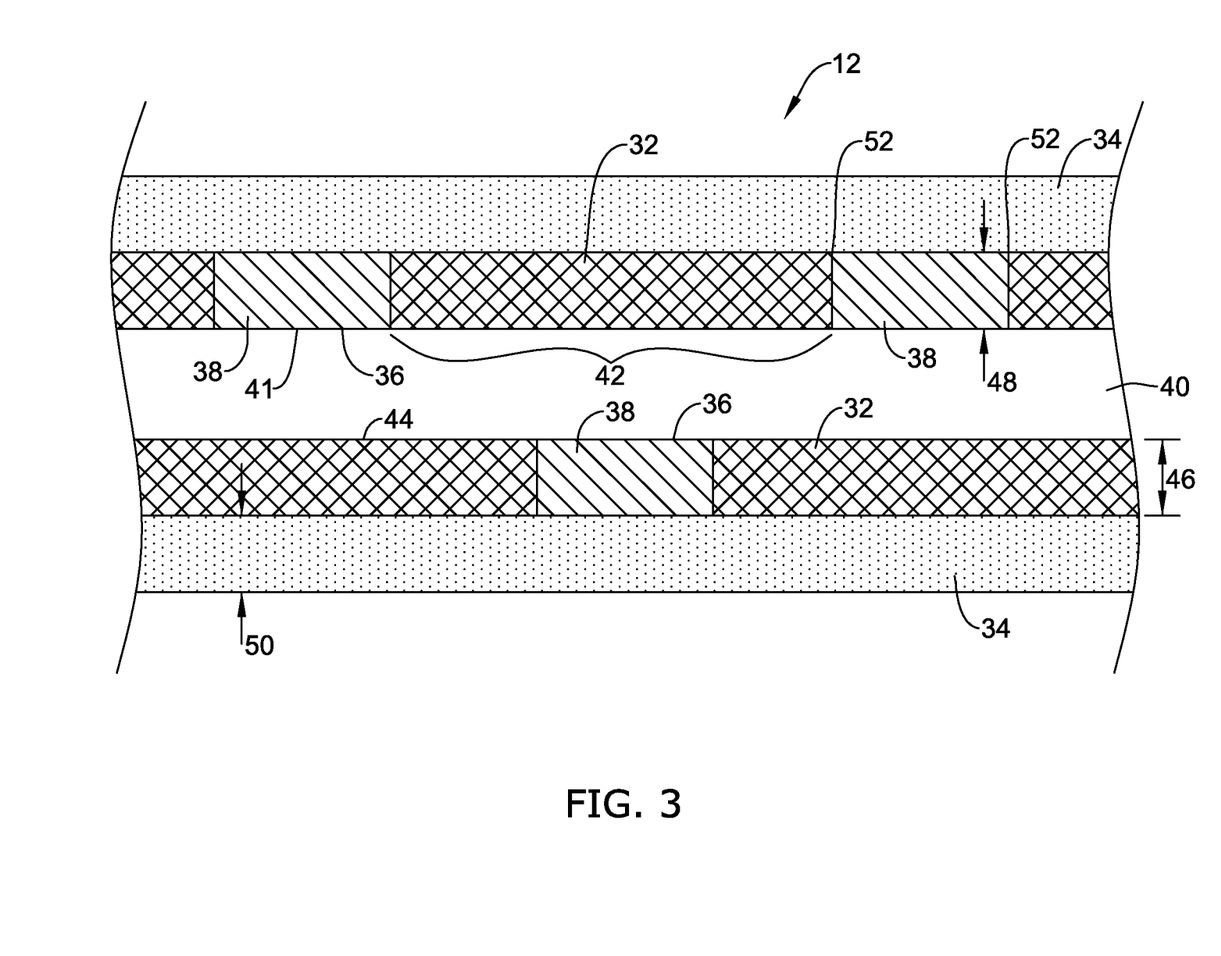
FIG. 3 is a partial sectioned view of the medical device of FIG. 2 taken along line 3-3.

FIG. 3 is a partial longitudinal cross-sectional view of the elongate tubular shaft 12, taken along line 3-3 of FIG. 2. The elongate tubular shaft 12 may be a generally tubular member defining a lumen 40 through which a guidewire (not explicitly shown) or other medical device (not explicitly shown) or fluid may be passed. The elongate tubular shaft 12 may include a strain relief layer 32 and an outer jacket 34. A support member 36 may be embedded in or otherwise disposed within the strain relief layer 32. It is contemplated that the support member 36 may be incorporated into any portion of the elongate tubular shaft 12 desired. For example, the support member 36 may be incorporated into an entire length of the elongate tubular shaft 12, the proximal portion 14, the intermediate portion 30, the distal portion 16, or combinations thereof.

The support member 36 may be a reinforcing layer configured to provide kink resistance while retaining a desired flexibility. In some embodiments, the support member 36 may be a helically wound coil, as shown in FIG. 3. In other embodiments, the support member 36 may take the form of a braid or other support member. The support member 36 can be formed of any suitable material, including metals and metal alloys, such as, but not limited to nitinol, stainless steel, tungsten, gold, titanium, silver, copper, platinum, or iridium. The support member 36 can also be formed from non-metallic material such as KEVLAR® (poly paraphenylene terephthalamide) fibers, LCP (liquid crystal polymer) fibers, glass fibers, etc. In at least some embodiments, portions or all of the support member 36 can include a radiopaque material. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted. For example, to enhance compatibility with Magnetic Resonance Imaging (MM) machines, it may be desirable to make support member 36, or other portions thereof, in a manner that would impart a degree of MRI compatibility. For example, the support member 36 or portions thereof may be made of a material that does not substantially distort the image and create substantial artifacts, which are gaps in the image. Certain ferromagnetic materials, for example, may not be suitable because they may create artifacts in an MM image. The support member 36 or portions thereof may also be made from a material that the MM machine can image. Some materials that exhibit these characteristics include, for example, tungsten, Elgiloy, MP35N, nitinol, and the like, and others.

It is contemplated that the support member 36 may include a wire, ribbon, or filament 38 that is wound into a helical configuration. When so provided, a braid may be formed by weaving or braiding together two or more filaments 38. Each filament 38 of braid may extend in a generally helical configuration with portions over or under the other filament 38. It is contemplated that the support member 36 may be formed from a single filament 38 or a plurality of filaments 38, as desired. In some instances, a plurality of filaments 38 may be wound together to be used as a single filament. The filament 38 may have any cross-sectional shape desired, such as, but not limited to, rectangular, circular, square, triangular, oblong, polygonal, etc. The filament 38 may be wound such that the support member 36 has an open pitch, a closed pitch, or combinations thereof. For example, FIG. 3 shows the filament 38 arranged such that there is space 42 between adjacent windings (e.g., the adjacent windings are not in contact). An open pitch configuration may be defined as space (e.g., such as the space 42 illustrated in FIG. 3 between windings on the same side of the tubular shaft 12) existing between adjacent windings of the filament 38. The absence of space between the windings may be referred to as a closed pitch configuration. A closed pitch configuration may be desirable to provide increased column strength to a given component of a medical device. Further, characteristics such as the filament cross-sectional dimension and/or shape, material, orientation and spacing may contribute to the overall configuration and performance (e.g., flexibility, pushability, trackability, column stiffness, etc.) of the support member 36.

The strain relief layer 32 may be disposed between adjacent windings of the support member 36 such that collectively the strain relief layer 32 and the support member 36 define or form an inner surface of the elongate tubular shaft 12. For example, the support member 36 may be formed by winding (or braiding) the filament 38 over a mandrel. The strain relief layer 32 may be applied between adjacent windings of the support member 36. When the strain relief layer 32 is applied between the adjacent windings of the support member 36, the strain relief layer 32 may be discontinuous along a plane of the longitudinal axis of the elongate tubular shaft 12 or have a generally helical configuration.

It is contemplated that the strain relief layer 32 may be applied so as to achieve a generally uniform thickness with the support member 36. For example, the strain relief layer 32 may have a thickness 46 that is approximately equal to a thickness 48 of the filament 38 in a radial direction. It is contemplated that having a uniform layer (e.g., the support member 36 and the strain relief layer 32) over which to apply the outer jacket 34 may increase the uniformity of the outer jacket 34. Increasing the uniformity of the outer jacket 34 may decrease localized strain. In other words, the strain across the outer jacket 34 may decrease the stresses in the outer jacket 34 as a uniform thickness 50 of the outer jacket 34 may cause elongation over an entire length of the outer jacket 34 instead of a shorter region (or reduced thickness) undergoing most of the elongation (which may occur if the outer jacket 34 is applied directly over the support member 36).

The strain relief layer 32 may be formed from a material having a modulus of elasticity that is less than a modulus of elasticity of the outer jacket 34. Said differently, the outer jacket 34 may be stiffer than the strain relief layer 32. In some cases, the strain relief layer 32 may be formed from an elastomeric material. An elastomeric material may be considered to be capable of achieving large and reversible elastic deformation. Some illustrative elastomeric materials may include, but are not limited to, urethane elastomers, elastomeric polyether block amides (e.g., elastomeric PEBAX®, having a durometer in the range of about 25D), polysiloxane (e.g., silicone), styrene-butadiene copolymer, elastomeric polyamides, acrylonitrile-butadiene copolymer, chloroprene, natural polyisoprene, etc. The strain relief layer 32 may be highly flexible. It is contemplated that when formed from a flexible, elastomeric material, the strain relief layer 32 may handle high strain rates without fracture from a geometry induced stress riser (e.g., the corners 52 of the filament 38 in contact with the outer jacket 34). Further, as described herein, the strain relief layer 32 may smooth out the transitional geometry between the support member 36 and the outer jacket 34. These features may create an effective strain relief between the support member 36 and the outer jacket 34 thus decreasing the localized strain seen by the outer jacket 34. This may significantly improve the bend radius that the elongate tubular shaft 12 can achieve before fracturing.

The outer jacket 34 may have a generally uniform diameter along a length of the elongate tubular shaft 12. The outer jacket 34 may be formed of one or more polymer and/or plastic materials along a length or thickness thereof. Some illustrative materials may include, but are not limited to polyether block amides (e.g., having a durometer in the range of 63D or greater), polyamides, polyurethanes, polyester/ethers, polyoxymethylene, blends, other high modulus polymers, etc. In some cases, the outer jacket 34 may include two materials having different material properties (e.g., durometer, tensile strength, etc.). It is also understood that the outer jacket 34 may include materials other than polymers or plastics. For example, the outer jacket 34 may include polymers, metals, ceramics, composites materials, combinations thereof, and the like.

The outer jacket 34 may be formed over or positioned on top of the strain relief layer 32 and support member 36 such that an inner diameter of the outer jacket 34 is approximately equal to the outer diameter of the strain relief layer 32 and support member 36. For example, the outer jacket 34 may be co-extruded over the strain relief layer 32 and the support member 36, or it can be pre-formed and then heat shrunk into position to form an outer surface of the elongate tubular shaft 12.

The medical device 10 may optionally include a coating layer such as a lubricious coating layer over part or all of an outer surface of the medical device 10 and/or an inner surface of the lumen 40. Suitable lubricious polymers are well known in the art and can include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

Figure 4A:
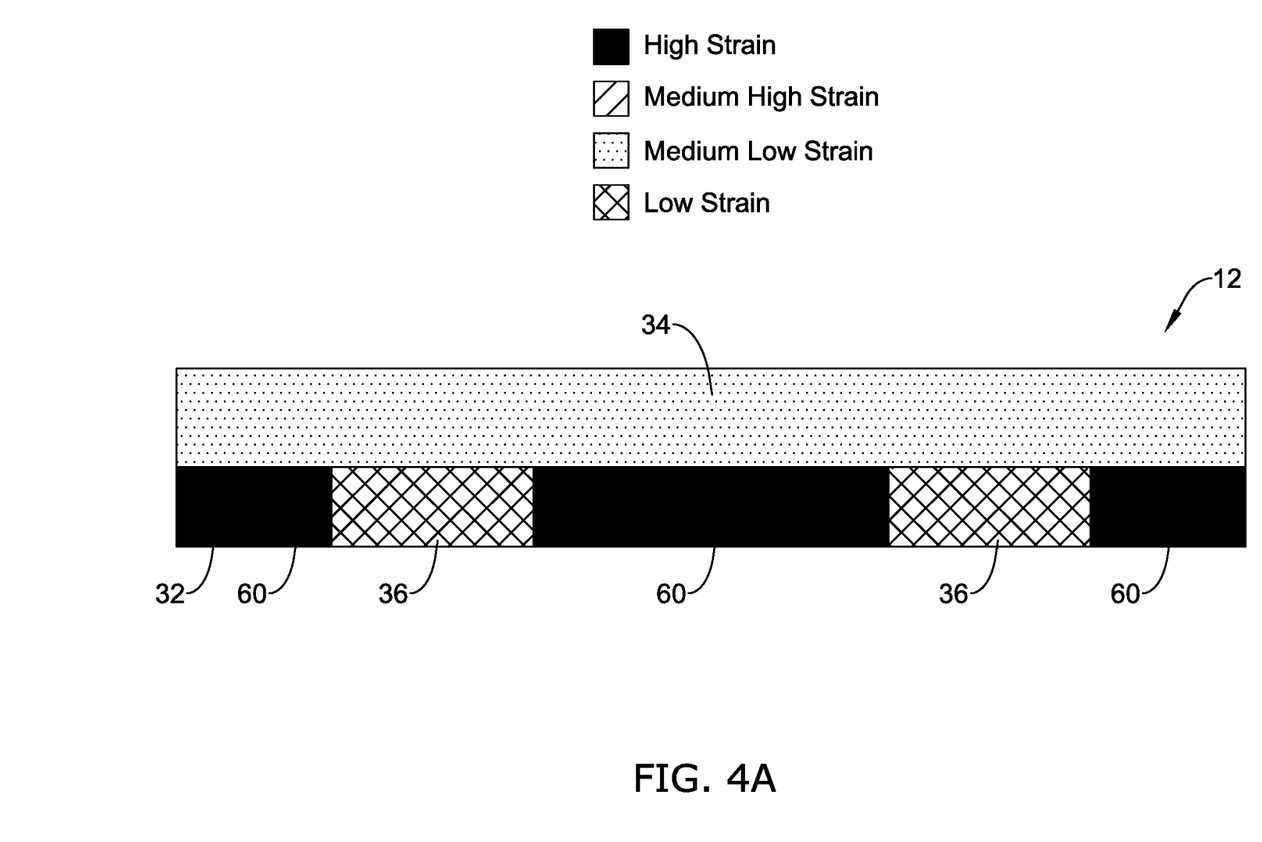
FIG. 4A is a schematic finite element analysis (FEA) of strain in the elongate tubular shaft of FIG. 3.
Figure 4B:
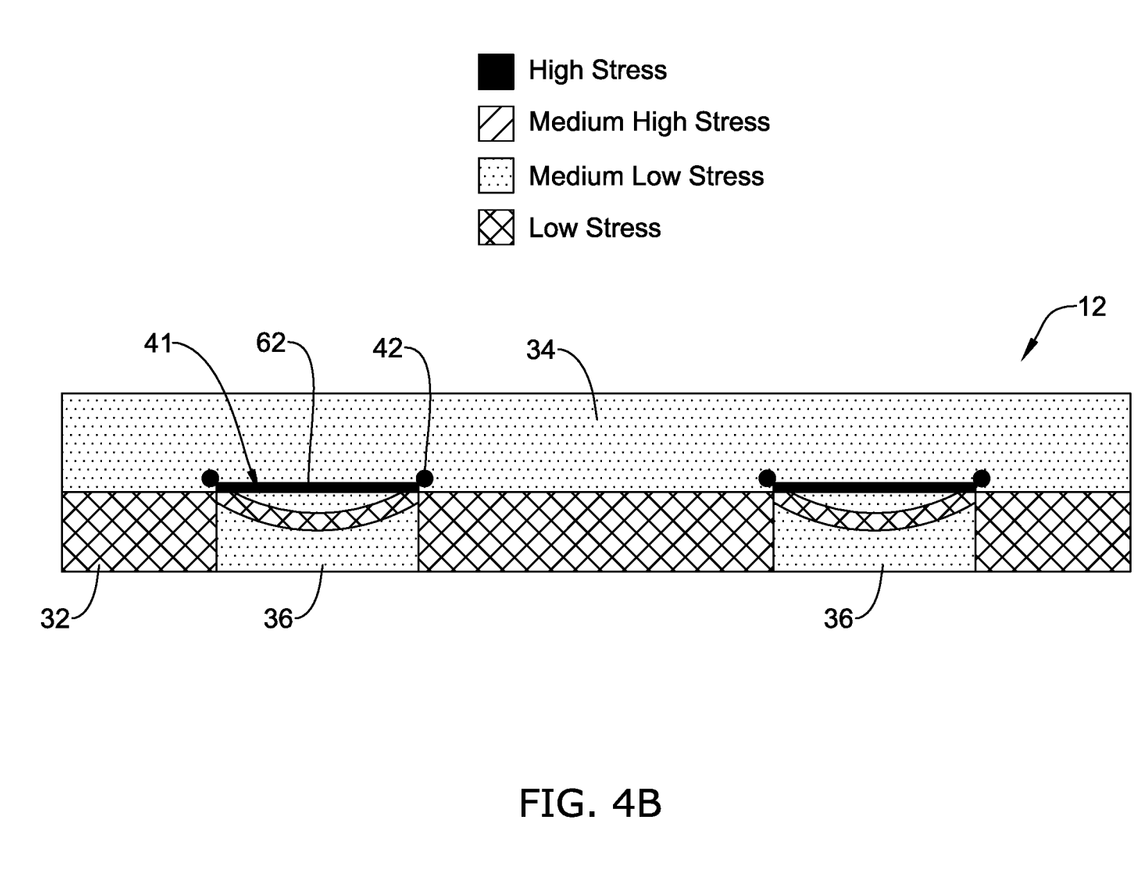
FIG. 4B is a schematic finite element analysis (FEA) of stress in the elongate tubular shaft of FIG. 3.

FIG. 4A is a schematic finite element analysis (FEA) of strain in the elongate tubular shaft 12 of FIG. 3 which includes a strain relief layer 32, an outer jacket 34, and a high modulus support member 36. FIG. 4B is a schematic FEA of stress in the elongate tubular shaft 12 of FIG. 3 which includes a strain relief layer 32, an outer jacket 34, and a high modulus support member 36. As can be seen in FIG. 4A, the highest strain 60 generally occurs in the strain relief layer 32 (e.g., the elastomeric layer). As can be seen in FIG. 4B, the highest stress 62 generally occurs within the outer jacket 34 along a radially outward surface 41 of the support member 36. FIGS. 4A and 4B illustrate strain relief between the support member 36 and the outer jacket 34 is obtained by decreasing localized strain within the outer jacket 34. This is in contrast to localized strain (e.g., areas of high strain 8 illustrated in FIG. 1B) shown in the FEA of the catheter 1 of FIG. 1A which does not include a strain relief layer.

Figure 5:
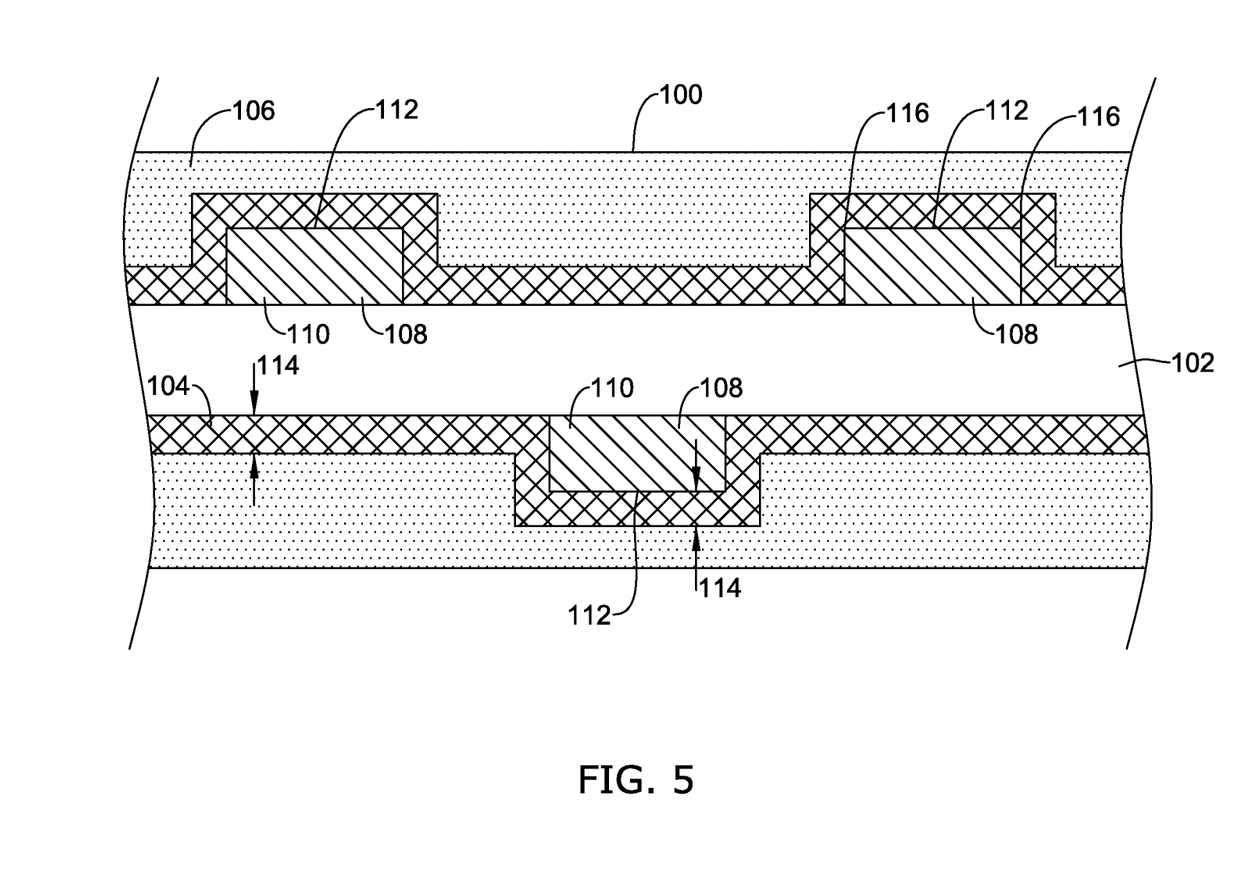
FIG. 5 is a partial sectioned view of another illustrative medical device.

FIG. 5 is a partial longitudinal cross-sectional view of another illustrative elongate tubular shaft 100 that may be used in the medical device 10 of FIG. 2. The elongate tubular shaft 100 may be a generally tubular member defining a lumen 102 through which a guidewire (not explicitly shown) or other medical device (not explicitly shown) may be passed. The elongate tubular shaft 100 may include a strain relief layer 104 and an outer jacket 106. A support member 108 may be embedded in or otherwise disposed within the strain relief layer 104. It is contemplated that the support member 108 may be incorporated into any portion of the elongate tubular shaft 100 desired. For example, the support member 108 may be incorporated into an entire length of the elongate tubular shaft 100, a proximal portion, an intermediate portion, a distal portion, or combinations thereof.

The support member 108 may be a helically wound coil, as shown in FIG. 5. In other embodiments, the support member 108 may take the form of a braid or other support member. The support member 108 can be formed of any suitable material, including metals and metal alloys, such as, but not limited to nitinol, stainless steel, tungsten, gold, titanium, silver, copper, platinum, or iridium. The support member 108 can also be formed from non-metallic material such as KEVLAR® (poly paraphenylene terephthalamide) fibers, LCP (liquid crystal polymer) fibers, glass fibers, etc. In at least some embodiments, portions or all of the support member 108 can include a radiopaque material. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted. For example, to enhance compatibility with Magnetic Resonance Imaging (MM) machines, it may be desirable to make support member 108, or other portions thereof, in a manner that would impart a degree of MRI compatibility. For example, the support member 108 or portions thereof may be made of a material that does not substantially distort the image and create substantial artifacts, which are gaps in the image. Certain ferromagnetic materials, for example, may not be suitable because they may create artifacts in an MRI image. The support member 108 or portions thereof may also be made from a material that the MRI machine can image. Some materials that exhibit these characteristics include, for example, tungsten, Elgiloy, MP35N, nitinol, and the like, and others.

It is contemplated that the support member 108 may include a wire, ribbon, or filament 110 that is wound into a coiled configuration. The filament 110 may have any cross-sectional shape desired, such as, but not limited to, rectangular, circular, square, triangular, oblong, polygonal, etc. The filament 110 may be wound such that the support member 108 has an open pitch, a closed pitch, or combinations thereof. Further, characteristics such as the filament cross-sectional dimension and/or shape, material, orientation and spacing may contribute to the overall configuration and performance (e.g., flexibility, pushability, trackability, column stiffness, etc.) of the support member 108.

The strain relief layer 104 may be disposed between adjacent windings of the support member 108 and over a radially outward surface 112 of support member 108 such that the strain relief layer 104 has a generally uniform thickness along a length of the elongate tubular shaft 100. The strain relief layer 104 may be disposed between adjacent windings of the support member 108 such that collectively the strain relief layer 104 and the support member 108 define or form an inner surface of the elongate tubular shaft 100. For example, the support member 108 may be formed by winding (or braiding) the filament 110 over a mandrel. The strain relief layer 104 may be applied between adjacent windings of the support member 108 and on the radially outward surface 112 thereof. When the strain relief layer 104 is applied between adjacent windings and on the radially outer surface 112 of the support member 108, the strain relief layer 104 may be a generally continuous layer along a plane of the longitudinal axis of the elongate tubular shaft 100. In some cases, the strain relief layer 104 may be applied as a separate layer in an extrusion or solution coating process. In other embodiments, the strain relief layer 104 may be formed by reflowing a bilayer extrusion onto the support member 108.

It is contemplated that the strain relief layer 104 may be applied so as to achieve a generally uniform thickness 114 along its length. The strain relief layer 104 may be formed from an elastomeric material. An elastomeric material may be considered to be capable of achieving large and reversible elastic deformation. Some illustrative elastomeric materials may include, but are not limited to, urethane elastomers, elastomeric polyether block amides (e.g., elastomeric PEBAX®), polysiloxane (e.g., silicone), styrene-butadiene copolymer, elastomeric polyamides, acrylonitrile-butadiene copolymer, chloroprene, natural polyisoprene, etc. The strain relief layer 104 may be highly flexible. It is contemplated that when formed from a flexible, elastomeric material, the strain relief layer 104 may handle high strain rates without fracture from a geometry induced stress riser (e.g., the corners 116 of the filament 110 in contact with the outer jacket 106). Further, the strain relief layer 104 may smooth out the transitional geometry between the support member 108 and the outer jacket 106. These features may create an effective strain relief between the support member 108 and the outer jacket 106 thus decreasing the localized strain seen by the outer jacket 106. This may significantly improve the bend radius that the elongate tubular shaft 100 can achieve before fracturing.

The outer jacket 106 may have a thickness that varies along a length of the elongate tubular shaft 100. For example, the outer jacket 106 may be thinner over the support member 108 that other regions. The outer jacket 106 may be formed of one or more polymer and/or plastic materials along a length or thickness thereof. Some illustrative materials may include, but are not limited to polyether block amides (e.g., having a durometer in the range of 63D or greater), polyamides, polyurethanes, polyester/ethers, polyoxymethylene, blends, other high modulus polymers, etc. In some cases, the outer jacket 106 may include two materials having different material properties (e.g., durometer, tensile strength, etc.). It is also understood that the outer jacket 106 may include materials other than polymers or plastics. For example, the outer jacket 106 may include polymers, metals, ceramics, composites materials, combinations thereof, and the like.

The outer jacket 106 may be formed over or positioned on top of the strain relief layer 104 and support member 108 such that an inner diameter of the outer jacket 106 is approximately equal to the outer diameter of the strain relief layer 104 and support member 108. For example, the outer jacket 106 may be co-extruded over the strain relief layer 104 and the support member 108, or it can be pre-formed and then heat shrunk into position to form an outer surface of the elongate tubular shaft 100.

Figure 6A:
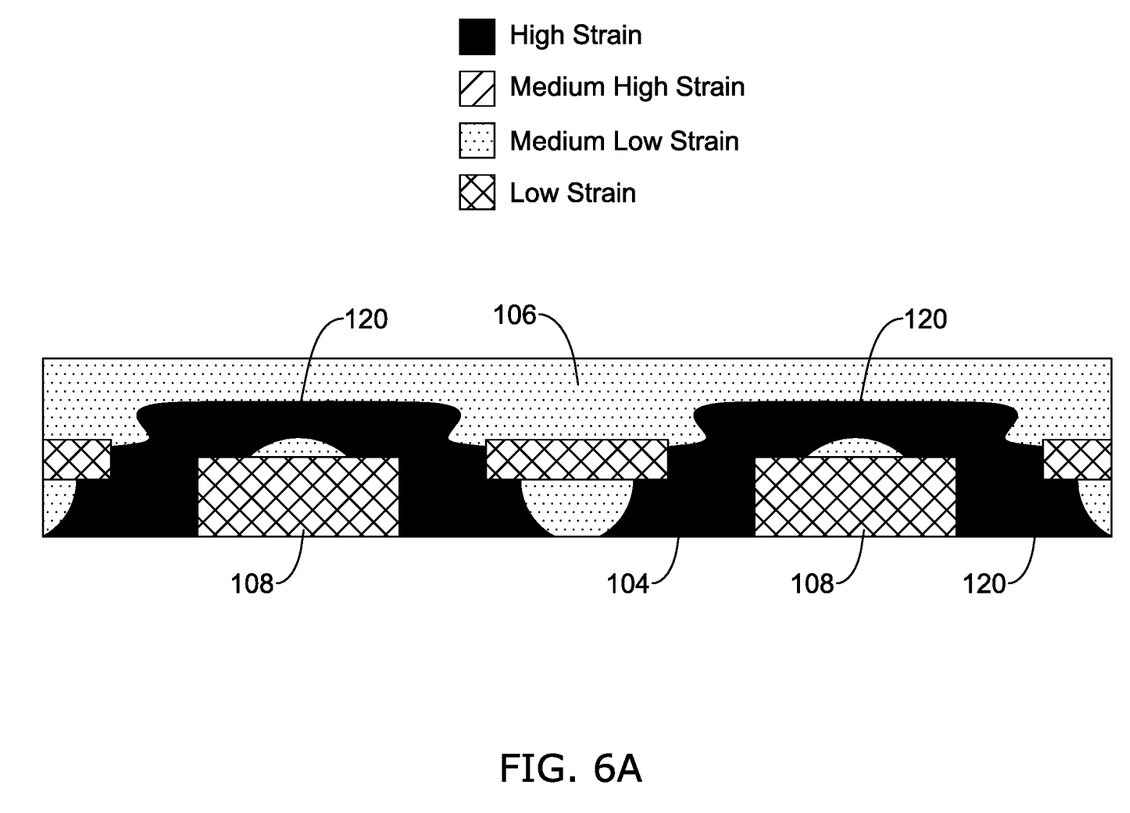
FIG. 6A is a schematic finite element analysis (FEA) of strain in the elongate tubular shaft of FIG. 5.
Figure 6B:
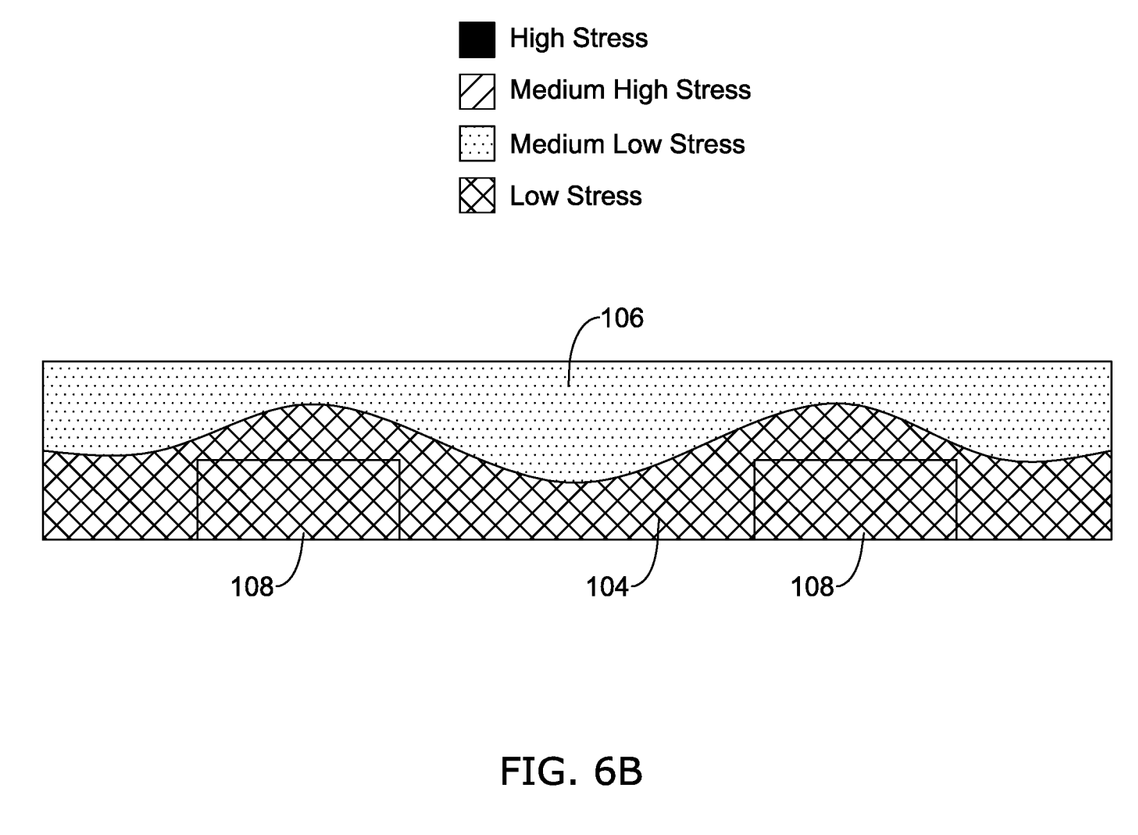
FIG. 6B is a schematic finite element analysis (FEA) of stress in the elongate tubular shaft of FIG. 5.

FIG. 6A is a schematic finite element analysis (FEA) of strain in the elongate tubular shaft 100 of FIG. 5, which includes a strain relief layer 104, an outer jacket 106, and a high modulus support member 108. FIG. 6B is a schematic FEA of stress in the elongate tubular shaft 100 of FIG. 5, which includes a strain relief layer 104, an outer jacket 106, and a high modulus support member 108 of FIG. 5. As can be seen in FIG. 6A, the highest strain 120 generally occurs in the strain relief layer 104 (e.g., the elastomeric layer). As can be seen in FIG. 6B, high stress has been significantly reduced, with the FEA showing none of the highest levels of stress shown in the embodiment illustrated in FIG. 1B. FIGS. 6A and 6B illustrate strain relief between the support member 108 and the outer jacket 106 is obtained by decreasing localized strain within the outer jacket 106.

In some embodiments, the medical device 10, the elongate tubular shaft 12, 100, and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

In at least some embodiments, portions or all of the medical device 10, the elongate tubular shaft 12, 100, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device 10, the elongate tubular shaft 12, 100, and/or components thereof, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10, the elongate tubular shaft 12, 100, and/or components thereof, etc. to achieve the same result.

In some embodiments, a degree of Magnetic Resonance Imaging (MM) compatibility is imparted into the access and anchor devices the medical device 10, the elongate tubular shaft 12, 100, and/or components thereof, etc. For example, the medical device 10, the elongate tubular shaft 12, 100, and/or components thereof, may be made of a material that does not substantially distort the image and create substantial artifacts (e.g., gaps in the image). Certain ferromagnetic materials, for example, may not be suitable because they may create artifacts in an Mill image. The medical device 10, the elongate tubular shaft 12, 100, and/or components thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device 10, the elongate tubular shaft 12, 100, and/or components thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device 10, the elongate tubular shaft 12, 100, and/or components thereof, etc. may include and/or be treated with a suitable therapeutic agent.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:
1. A medical device, comprising:
an elongate tubular shaft defining a lumen extending from a proximal portion to a distal portion, the elongate tubular shaft comprising:

an outer jacket forming an outer surface of the elongate tubular shaft;

a support member including at least one filament extending in a helical configuration along at least a portion of a length of the elongate tubular shaft;

a strain relief layer comprising a material that has a modulus of elasticity less than a modulus of elasticity of the outer jacket, the strain relief layer positioned at least between adjacent windings of the support member and over a radially outward surface of the at least one filament;

wherein the strain relief layer and the support member collectively form an inner surface of the elongate tubular shaft;

wherein the strain relief layer has a first thickness defining the inner surface of the elongate tubular shaft between the adjacent windings of the at least one filament and a second thickness on the radially outward surface of the at least one filament, wherein the first and second thicknesses are the same;

wherein the outer jacket has a first thickness where the outer jacket overlies the strain relief layer positioned over a radially outward surface of the at least one filament; and wherein the outer jacket has a second thickness greater than the first thickness where the outer jacket overlies the strain relief layer positioned between adjacent windings of the at least one filament.

2. The medical device of claim 1, wherein the strain relief layer comprises an elastomeric urethane.

3. The medical device of claim 1, wherein the strain relief layer comprises an elastomeric polyether block amide.

4. The medical device of claim 1, wherein the outer jacket comprises a polyamide or a polyether block amide having a durometer of about 63D or greater.

* * * * *